Figure 1:
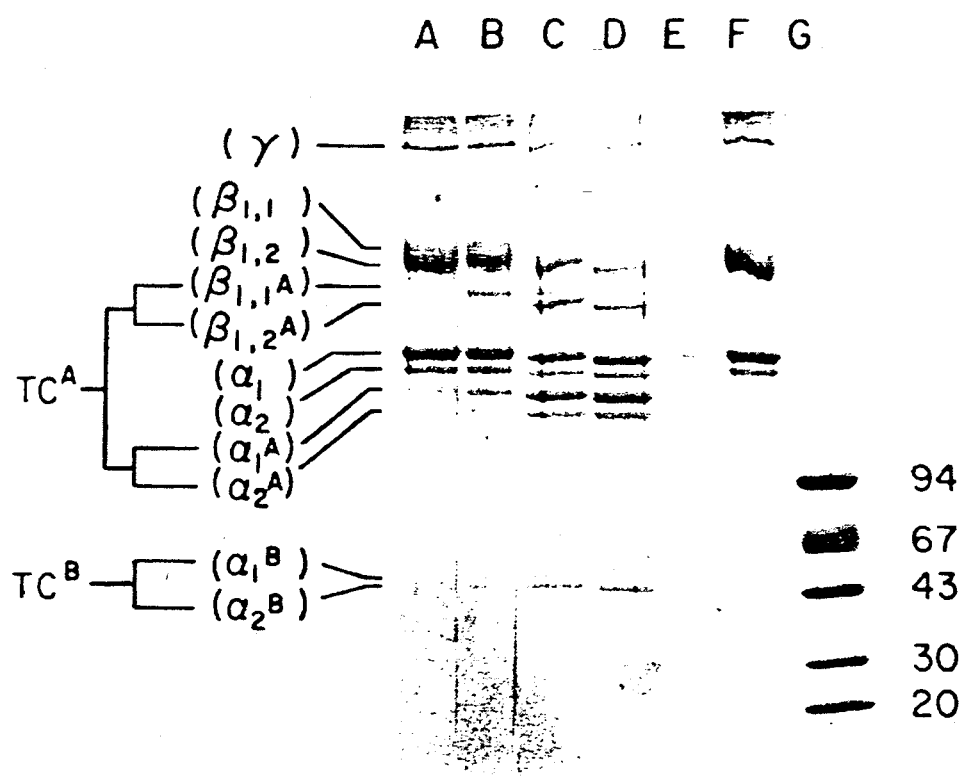

United States Patent [19]

Sawyer et al.

US005139944A

[11] Patent Number: 5,139,944
[45] Date of Patent: Aug. 18, 1992

[54] COLLAGEN-SPECIFIC ENZYME WITH PLATELET AGGREGATION INHIBITION PROPERTIES

[75] Inventors: Roy T. Sawyer, Swansea, United Kingdom; Meir Rigbi, Jerusalem, Israel; Haim Levy, Jerusalem, Israel; Fuad Iraqi, Jerusalem, Israel

[73] Assignees: Biophram (UK) Limited, West Glamorgan, United Kingdom; Yissum Research Development Company of the Hebrew University of Jerusalem, Jerusalem, Israel

[21] Appl. No.: 647,652
[22] PCT Filed: Aug. 11, 1986
[86] PCT No.: PCT/GB86/00481
  § 371 Date: May 29, 1987
  § 102(e) Date: May 29, 1987
[87] PCT Pub. No.: WO87/00860
  PCT Pub. Date: Feb. 12, 1987

Related U.S. Application Data

[63] Continuation of Ser. No. 41,016, Apr. 10, 1987, abandoned.

[30] Foreign Application Priority Data

Aug. 10, 1985 [GB] United Kingdom ............... 8520121
Jul. 11, 1986 [GB] United Kingdom ............... 8616900

[51] Int. Cl.$^5$ ............................................. C12N 9/64
[52] U.S. Cl. .................................................. 435/226
[58] Field of Search ......................................... 435/226

[56] References Cited

U.S. PATENT DOCUMENTS 3,646,195  2/1972  Eriksson et al. ............. 424/94
4,390,630  6/1983  Sawyer et al. .............. 435/226
4,588,587  5/1986  Gasic ......................... 424/95
4,788,149  11/1988  Cerami et al. .............. 435/212

FOREIGN PATENT DOCUMENTS 2216992  9/1974  France .

OTHER PUBLICATIONS

Stricklin et al. Biochemistry vol. 16 #8, 1977 p. 1607 Human Skin Collagenase: Isolation of Precursor and Active Forms From Both Nibroblast and Organ Cultures.

Primary Examiner—Richard A. Schwartz
Assistant Examiner—S. Nolan
Attorney, Agent, or Firm—Darby & Darby

[57] ABSTRACT

The collagenase is like tissue collagenases in that it cleaves collagen at a single site. The collagenase which has a molecular weight of about 50 k daltons, specifically inhibits collagen-induced platelet aggregation, with substantially no effect on platelet count or size, and may be used alone or together with another platelet aggregation inhibitor. The latter may also be a leech-derived biochemical, such as an apyrase, or an inhibitor of the release of platelet aggregation factor by leucocytes.

4 Claims, 5 Drawing Sheets

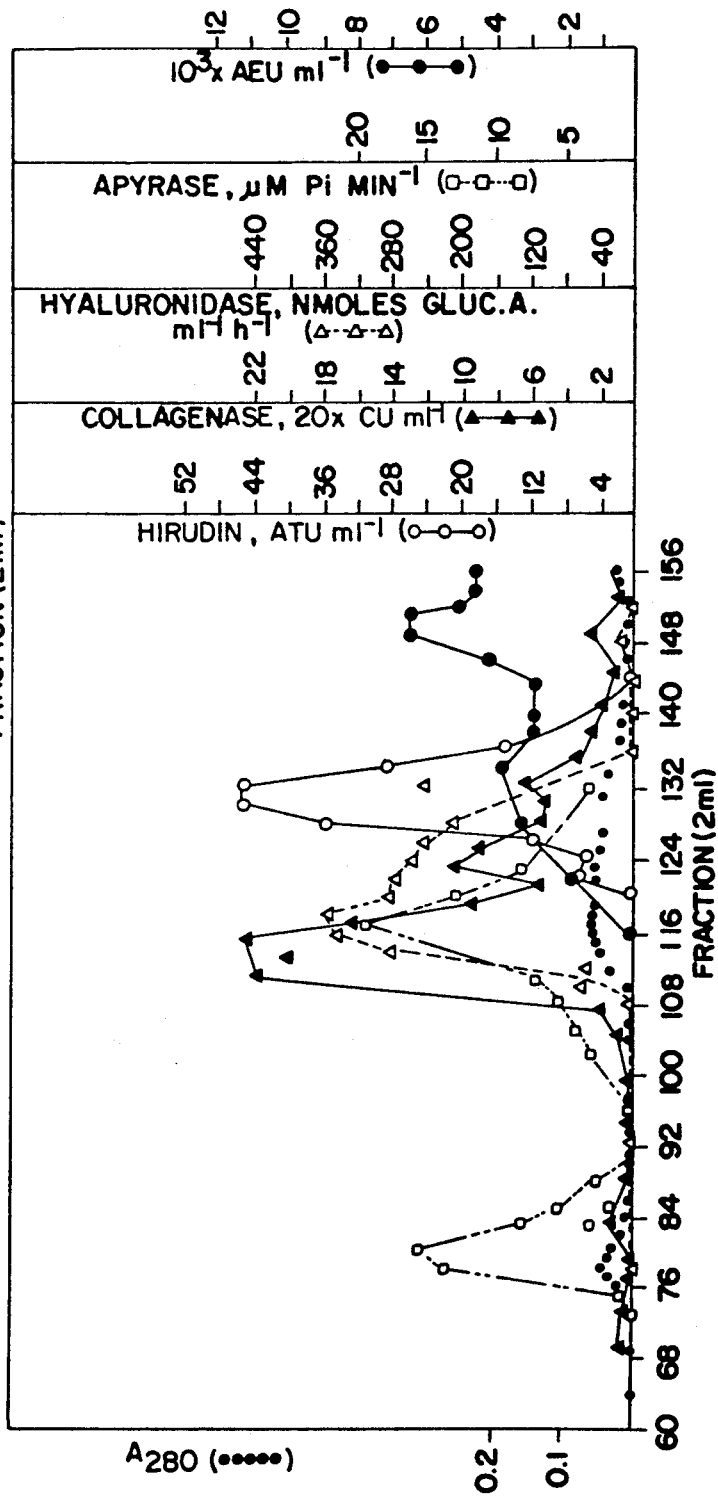
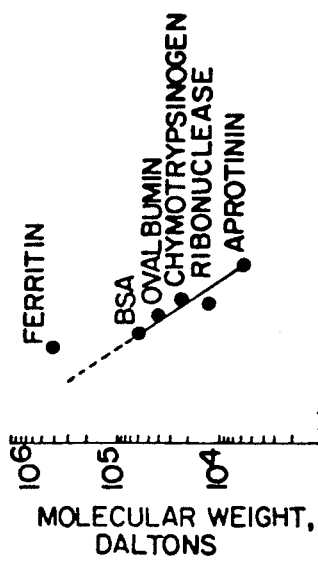
FIG. 2a
FIG. 2b

COLLAGEN-SPECIFIC ENZYME WITH PLATELET AGGREGATION INHIBITION PROPERTIES

This is a continuation of application Ser. No. 041,016, filed Apr. 10, 1987, now abandoned.

The present invention is concerned with collagen-specific enzymes with platelet aggregation inhibition properties; for brevity we will refer to such enzymes herein as collagenases.

The name collagenase is used for an important group of enzymes which specifically degrade collagen by means of hydrolytic scissions of peptide bonds in the helical regions when the collagen is in the native (undenatured) state. There are basically two types of collagenases:

(a) those making multiple non-specific hydrolytic scissions of the collagen molecule. This type of collagenase is elaborated by micro organisms that in themselves do not contain collagen;

(b) those which make a very limited number, typically one cut, per collagen molecule. This type of collagenase, the so-called tissue collagenases, is produced by mammals and other advanced animals that in fact have collagen as a major extracellular component of their tissues (Harris, E. D. and E. C. Cartwright 1977 in, Proteinases in Mammalian Cells and Tissues, Elsevier, pp 249-282).

Collagen is a structural protein which is virtually ubiquitous throughout the human body and bodies of higher animals. It is characterized by regions of small, repeating sequences of amino acids which result in the formation of helical chains between molecules. These helices give rise to its exceptional structural stability and strength. As a major constituent of connective tissue and skin, and the extracellular matrix (cement) which binds cells together, and as a major trigger in the aggregation of platelets collagen is of considerable physiological importance. An enzyme which specifically cleaves collagen should have a wide variety of medical and scientific applications.

Collagenases are widely distributed in nature in, for example, bacteria and vertebrate tissue. Bacterial collagenases, e.g. those produced by *Clostridium histolyticum*, are of the first type; that is, they cleave the collagen molecule at approximately 200 sites. This type is concerned with invasion of a host and, through degradation of the collagen molecule, with nutrition. Mammalian and other vertebrate collagenases are of the second type; that is, they cleave collagen at only one specific site. This type is concerned with repair of tissues, removing injured collagen, and remodelling of specialized tissues at a particular time of development or physiological expression, e.g. resorption of the tadpole tail or involution of the postpartum uterus. Following biochemical extraction and purification, tissue collagenases occur in latent form which requires specific activation. Harris, E. D. and E. C. Cartwright 1977, in, *Proteinases in Mammalian cells and tissues*, Elsevier, pp 249-282; Cawston, T. E. and G. Murphy 1981. *Methods Enzymol* 80, pp 711-734. This property severely limits the commercial usefulness of the known tissue collagenases. In fact relatively little is known about tissue collagenase because of the technical difficulties of having active enzyme in pure form.

This invention is concerned with a new type of tissue collagenase which occurs in active form following extraction. This active type of collagenase can be derived from the cephalic tissue of leeches. We have now isolated this new type of tissue collagenase from a variety of arhynchobdellid and rhynchobdellid leech species, including members of the family Hirudinidae, e.g. *Hirudo medicinalis*, *Hirudinaria manillensis* and *Poecilobdella granulosa*; the family Haemadipsidae e.g. *Haemadipsa zeylanica* and *Haemadipsa picta*; and the family Glossiphoniidae, e.g. *Haementeria ghilianii* (all the above being as defined in "Leech Biology and Behaviour" by Dr. R. T. Sawyer, Oxford University Press, 1986).

According to the invention, therefore, there is provided a collagenase which is such that it cleaves native (undenatured) collagen at a single site, said collagenase being characterised by the fact that it is leech derived.

The leech collagenase according to the invention belongs to the tissue type of collagenases in that it cleaves at a single primary site of the collagen molecule. By way of example, the action of leech collagenase on Type I collagen from calf skin is revealed by SDS-PAGE to result in the progressive cleavage of α chains into large $\alpha^A$ and small $\alpha^B$ fragments (FIG. 1). The same example demonstrates that leech collagenase, unlike tissue collagenases from mammals and other vertebrates, occurs in active form.

The leech collagenase according to the invention inhibits the collagen-induced aggregation of platelets (or thrombocytes) in vitro, while having substantially no effect on either platelet count or platelet size. This activity is highly specific, and is not due to some indirect effect but due to a direct effect on the induction of platelet aggregation by collagen. (Bacterial collagenase, in contrast, does not inhibit platelet aggregation).

It is known that collagen is an activator of two mechanisms of platelet aggregation. In a first mechanism, known as the arachidonic acid pathway, collagen stimulates phospholipase $A_2$ within the platelets; this reaction in turn releases arachidonic acid which is converted through the action of cyclo-oxygenase enzyme to thromboxane $A_2$. The latter mobilises intraplatelet calcium and causes release from the platelet granules of other proteins, such as serotonin and platelet derived growth factor, and also releases nucleotides such as adenosine diphosphate (ADP).

In a second mechanism, subendothelial collagen and thrombin activate the platelets, granule release of calcium occurs, and also release of platelet derived growth factor 4, and the platelets adhere directly to the subendothelium.

The action of the leech collagenase according to the invention is to inhibit platelet aggregation which proceeds along either of these two mechanisms.

The leech-derived collagenase according to the invention is further characterized by the following properties:

(a) It comprises a polypeptide of molecular weight 50,000±5,000, when measured by gel chromatography using Fractogel TSK HW (55F) (FIG. 2);

(b) It appears to retain significant activity after solvent extraction whereas mammalian-type collagenase does not;

(c) It readily digests native collagen and denatured collagen (gelatin).

The leech collagenase according to the invention has a large number of potential uses, for example, as follows:

(a) as a research biochemical, for example for the study of native collagen and its relationship to other extracellular components, and the identification, characterisation and quantification of collagen;

(b) for use in tissue culture, for example, for dissociating tissue, such as leech collagenase-digested cells for the production of vaccines and the like;

(c) as a research tool for inhibiting platelet aggregation in vivo, for use in studying the mechanism of collagen-induced platelet aggregation and thromboses;

(d) in the treatment of hide, fur, meat (for example, to soften hide or fur, tenderize meat or treat sausage casings or the like).

(e) for recovery of silver from photographic waste; and (f) for use in therapy.

In connection with use in therapy, the leech collagenase according to the invention may have the following uses:

1. selective degradation of collagen in the eye to remove scar tissue (for example, after cataract surgery, retinal detachment and pars plana vitretomy);

2. removal of necrotic tissue produced by ulcers or burns and to induce growth of normal tissue;

3. treatment and prevention of cicatrices (such as acne scars, keloids, wrinkles and cellulitis);

4. enhancement of penetration of a pharmaceutically active material through the skin (optionally together with leech-derived hyalurodinase as described in European Patent Specification 193330);

5. treatment of dental transplants and root canals, for removal of odontoblasts for example;

6. treatment of herniated intervertabral discs by injection;

7. stimulation or inhibition of angiogenesis;

8. treatment of Peyronie's disease by administration of the collagenase directly on to the plaques which form in the course of the disease; and 9. inhibition of platelet aggregation in vivo.

In connection with the latter, many synthetically produced chemicals used as inhibitors of platelet aggregation (such as dipyridamole, aspirin, sulphinpyrazone, ticlopidine, prostacyclin and thromboxane synthetase inhibitor) are non-specific and affect many metabolic processes in addition to platelet aggregation. The leech collagenase according to the invention has less undesirable side-effects (presumably because it has evolved biologically to do as little damage to the host's body as possible) and acts directly on one of the fundamental inducers of platelet aggregation.

The use of collagenase for the inhibition of platelet aggregation (in vivo or in vitro) is a very important aspect of the present invention. As far as we are aware, no-one has previously suggested the use of tissue-type collagenase (that is collagenase which cleaves collagen at a single site) for this purpose and according to a further aspect of the present invention, therefore, there is provided collagenase which cleaves collagen at a single site for use in the inhibition of platelet aggregation.

In this connection, the collagenase may be used (alone or together with other active factors) for the following purposes.

(i) in micro-surgery to induce prolonged localised bleeding and to restore blood circulation in congested implants or skin or tissue flaps;

(ii) as a prophylactic treatment of transplanted tissue, such as veins used in coronary by-pass surgery, to prevent collagen-associated platelet aggregation;

(iii) to reduce the risk of post-surgical clots by denaturing raw collagen exposed to blood, by treatment of collagenase at the site of surgery and by circulation of collagen in the blood to inactivate exposed collagen;

(iv) to reduce aggregation of platelets along atheromatous plaques and along blood vessel fractures where collagen is exposed;

(v) to reduce the risk of platelet aggregation whenever a collagen-associated prosthesis or implant is employed.

The leech collagenase according to the invention may be employed in substantially pure form, or together with one or more further inhibitors of platelet aggregation (which inhibit platelet aggregation induced by the same or a different factor). It is sometimes desirable to employ the leech collagenase in conjunction with an inhibitor for other mechanisms of platelet aggregation. Several such inhibitors (believed to be novel per se) have been found to be present in leech saliva. Indeed, at least three such inhibitors have been found in leech saliva, one being an apyrase (an ADP-induced platelet aggregation inhibitor) of molecular weight approximately 400,000, a second being an apyrase of molecular weight approximately 45,000, and a third being an inhibitor of the release of platelet aggregation factor by leucocytes and having a molecular weight of about 600. The leech collagenase according to the invention may be used together with one or more such inhibitors.

In order that the present invention may be more fully understood the following Examples are given by way of illustration only.

EXAMPLE 1

Crude extract containing leech collagenase was collected from starved *Hirudo medicinalis* in the following manner. The leeches were allowed to feed through a dried calf intestine membrane on a solution of 0.1 mM arginine in saline. The ingested leech was then made to regurgitate, the regurgitant constituting the crude extract. Apart from collagenase the extract contained no other detectable proteases. This is in sharp contrast to the micro-organism derived collagenase, which was heavily contaminated with proteolytic enzymes.

The crude extract was fractionated with 0.2M ammonium bicarbonate on a 2×90 cm Fractogel TSK HW (55 F) column. The eluate was collected at 2 ml intervals at a flow rate of 41 ml per hour.

The fractions were assayed by incubating leech fraction with $^{125}$I-collagen-sepharose in 0.05% bovine serum albumin/5 mM $CaCl_2$/75 mM HEPES buffer, pH 7.5 for 5 hours at 25° C. Activity was measured by release of $^{125}$I from the Sepharose-bound collagen. One collagenase unit (CU) is that amount which degrades 1 μg of iodinated collagen-sepharose. The assay is linear over 5 hours.

Leech collagenase was found in peak fraction 115 (FIG. 2a). By comparison with markers of known molecular weight, the molecular weight of leech collagenase is taken to be approximately 50,000±5,000 daltons (FIG. 2b). Similar results were found with collagenase extracted from *Poecilobdella granulosa*.

EXAMPLE 2

The mechanism of cleavage of leech collagenase was determined as follows. Crude extract was prepared as per Example 1. The crude extract ($A_{280}$ 0.077) was incubated with Type I collagen (1 mg ml$^{-1}$) from calf skin in 1.5 mM $CaCl_2$/10 mM Tris-HCl buffer pH 7.8 (total volume 100 μl) at 37° C. for 1,5 and 24 hours. Collagen alone and clostridium collagenase (0.1 mg ml$^{-1}$) were used as controls. Solubilizing mixture (120 μl, Nature 227, p. 680) was then added and the mixtures were placed in a water bath for 3 minutes. 50 microliters of mixture were placed in each well of SDS-PAGE gel.

The results are presented in FIG. 1. Lanes A and F, collagen controls; B, C and D, crude extract incubated for 1, 5 and 24 hours respectively; E, clostridium collagenase incubated for 1 hour; G, molecular weight markers.

It may be seen that the isolated α chains are progressively cleaved into large $α^A$ fragments and small $α^B$ fragments. This highly specific cleavage pattern characterizes leech collagenase as a tissue type collagenase, and is in sharp contrast to the non-specific cleavage by collagenases from micro organisms. It can also be seen that, in contrast to the latent form of tissue collagenases from mammals, leech collagenase occurs in active form in the crude extract.

EXAMPLE 3

A sensitive assay for measuring tissue-type collagenase has been devised involving detection of collagenase inhibition of collagen-induced platelet aggregation.

(a) Tissue type collagenase (Human synovial fibroblast collagenase) (3 collagenase units or CU) and clostridium collagenase (50 μg, 12 CU) were examined for their effects on platelet aggregation. Tissue-type collagenase greatly reduced collagen-induced platelet aggregation whereas clostridium collagenase, at a four-fold concentration of collagenase units in the test mixture, was practically without effect.

The above demonstrates that the above assay is specific for tissue type collagenases.

(b) Crude leech extract was prepared and assayed as per Example 1. Apyrase was removed from the crude extract by passing it through a 0.2 ml GTP-agarose column washed with 1 mM arginine/saline. The apyrase-free extract strongly inhibits platelet aggregation induced by collagen. The measured leech collagenase activity was 2.25 collagenase units.

The above demonstrates that leech collagenase specifically inhibits collagen-induced platelet aggregation. In the above examples (a) and (b) Platelet Rich Plasma (PRP) (400 μl) HEPES buffer pH 7.35, and the test solution were pre-incubated for 1 minute, when 1.2 μg/ml collagen was added (final reaction volume 500 μl). Aggregation was followed by the increase in light transmission against time, as recorded on an aggregometer chart. $A_{280}$ values of the crude extract in the test mixtures ($\times 10^3$) were evaluated as platelet aggregometer tracings. The measured collagenase activity was 15.3 CU per 1.0 $A_{280}$.

(c) Crude leech extract (Stage I) from cephalic tissue of buffalo leeches was fractionated as follows. The head regions of 40 buffalo leeches *Poecilobdella granulosa* were removed and weighed (32.8 g fresh weight). They were homogenized in distilled water for ten minutes at 4° C. The suspension was centrifuged at 650 g for 10 minutes at 4° C. The supernatant is saved, while the precipitate is resuspended and centrifuged again. The supernatants are combined to give Stage I enzyme.

The effect of the isolated proteinacous material on platelet aggregation has been studied in vitro using platelet-rich plasma (PRP) produced by centrifuging fresh blood at 800 g for 5 minutes. The PRP produced was preincubated with isotonic leech extract of varying stages of purity. Controls were performed in which isotonic saline replaced the leech extract. After this pre-incubation the PRP was incubated with a variety of inducers of platelet aggregation, namely collagen, ADP and ristocetin.

Results are obtained using an EEL platelet aggregometer by measurement of the optical density of the incubated mixture with time, the mixture becoming less turbid as platelet aggregation occurs. A blank preparation of platelet-poor plasma was used to give an optical density value for a solution lacking platelets.

Stage I was fractionated on G75 Sephadex gel (1.6×75 cm). Elution was performed using 50 mM-Tris HCl, 20 mM NaCl, pH 7.0 at a rate of 1.0 ml per minute. Fractions were collected at 5 minute intervals and their protein content measured on a spectrophotometer by absorbance at 280 nm. Protein was eluted with peaks measured in Fractions 4 and 26. Each of the fractions collected, as well as the crude extract, were examined for inhibition of collagen-induced platelet aggregation as described above. Only fractions 4 and 26 as well as crude extract were found to contain activity capable of substantially inhibiting aggregation induced by 1 μg ml$^{-2}$ collagen. Fraction 26 contained collagenase activity. Fraction 4 contained apyrase activity (10 μg ml$^{-1}$ ADP).

The crude extract in serial dilution was found to inhibit significantly collagen induced platelet aggregation induced by 1 μg ml$^{-1}$ collagen at 0.1, 0.01 and 0.001 dilution.

The crude extract itself extensively inhibited platelet aggregation even at concentrations of collagen of 40 μg ml$^{-1}$ which is ten times higher than that normally used to induce platelet aggregation in vitro. Ristocetin-induced platelet aggregation was not inhibited by pre-incubation with leech extract according to the invention. Furthermore, leech extract does not affect platelet count nor platelet size. Also our finding that ADP-induced platelet aggregation is not totally blocked with leech apyrase or collagenase indicates another inhibitor of platelet aggregation is present in the leech.

The enzyme was further purified in the following manner. To the 40% supernatant containing the enzyme ammonium sulphate was added at 80% saturation. The suspension was centrifuged at 800 g for 20 minutes at 4° C. The pellet is resuspended in buffered solution and dialysed three times against distilled water at 4° C.

The resuspended 80% pellet was assayed by the sensitive technique described in Example 3 in which collagenase inhibits collagen-induced platelet aggregation. Platelet aggregation induced by collagen was found to be extensively inhibited by the 80% pellet.

The 80% supernatant had significantly reduced ability to inhibit collagen-induced platelet aggregation.

When assayed for collagenase activity, as per Example 4, the 80% pellet contained collagenase activity whereas the 80% supernatant did not.

That the 80% supernatant had some platelet inhibition but no collagenase might be interpreted as evidence for the presence of a low molecular weight inhibition of platelet aggregation in the 80% fraction, not collagenase. Further evidence is presented by the inhibition by the 80% supernatant but not the 80% pellet, of the secondary wave of aggregation in the presence of high (100 mg ml$^{-1}$) and medium (50 mg ml$^{-1}$) concentrations of ADP.

EXAMPLE 4

Leech collagenase was further characterized as follows:

The frozen head regions of buffalo leeches *Poecilobdella granulosa* were weighed (114 g fresh weight). The tissue was homogenized in distilled water for 10 minutes at 4° C. The suspension was centrifuged at 650 g for 10 minutes at 4° C. The supernatant was saved, while the precipitate was resuspended and centrifuged again. The supernatants were combined to give Stage I enzyme, total volume 146 ml. The enzyme was further purified by adding 40% saturated ammonium sulphate to Stage I supernatant. The suspension was centrifuged at 800 g for 20 minutes at 4° C. To the 40% supernatant was added 80% saturated ammonium sulphate. The suspension was centrifuged as before. The 80% pellet was suspended, to which was added 50% ammonium sulphate. Following dialysis against distilled water at 4° C., the Stage I enzyme, 40%, 80% and 50% pellets and supernatants were assayed for total protein and collagenase activity, respectively. Boiled Stage I served as control.

The fractions were assayed for collagenase activity by incubating 100 μl of each fraction in 100 μl of collagen (2% gelatin) for 24 hours. After incubation the solutions were placed onto ice for 30 minutes. Failure of the solution to gel upon cooling results from collagenase activity.

Results were as follows.

| | Collagenase Activity (% gelatine digested) | Protein |
| --- | --- | --- |
| Stage I | 100% | 24 mg/ml |
| 40% pellet | 100% | 12.6 mg/ml |
| 40% supernatant | 50% | 7 mg/ml |
| 80% pellet | 100% | 8 mg/ml |
| 80% supernatant | 0% | 0.12 mg/ml |
| 50% pellet | 50% | 16 mg/ml |
| 50% supernatant | 0% | 2.6 mg/ml |

It can be seen from the above experiment that leech collagenase is a molecule which is precipitated by both 80% ammonium sulphate and 50% ammonium sulphate. It can be dissolved in part in 40% ammonium sulphate.

A two ml sample of 50% ammonium sulphate pellet was extensively dialysed against 5 liters distilled water, made up to 1M-NaCl and then applied to a G75 superfine Sephadex column that had been equilibrated with 50 mM-Tris HCl, 20 mM-NaCl pH 7.5. The gel bed was 70 cm high and 1.6 cm in diameter with a flow rate of 20 ml per hour. Fractions were collected at 20 min. intervals.

Figure 3:
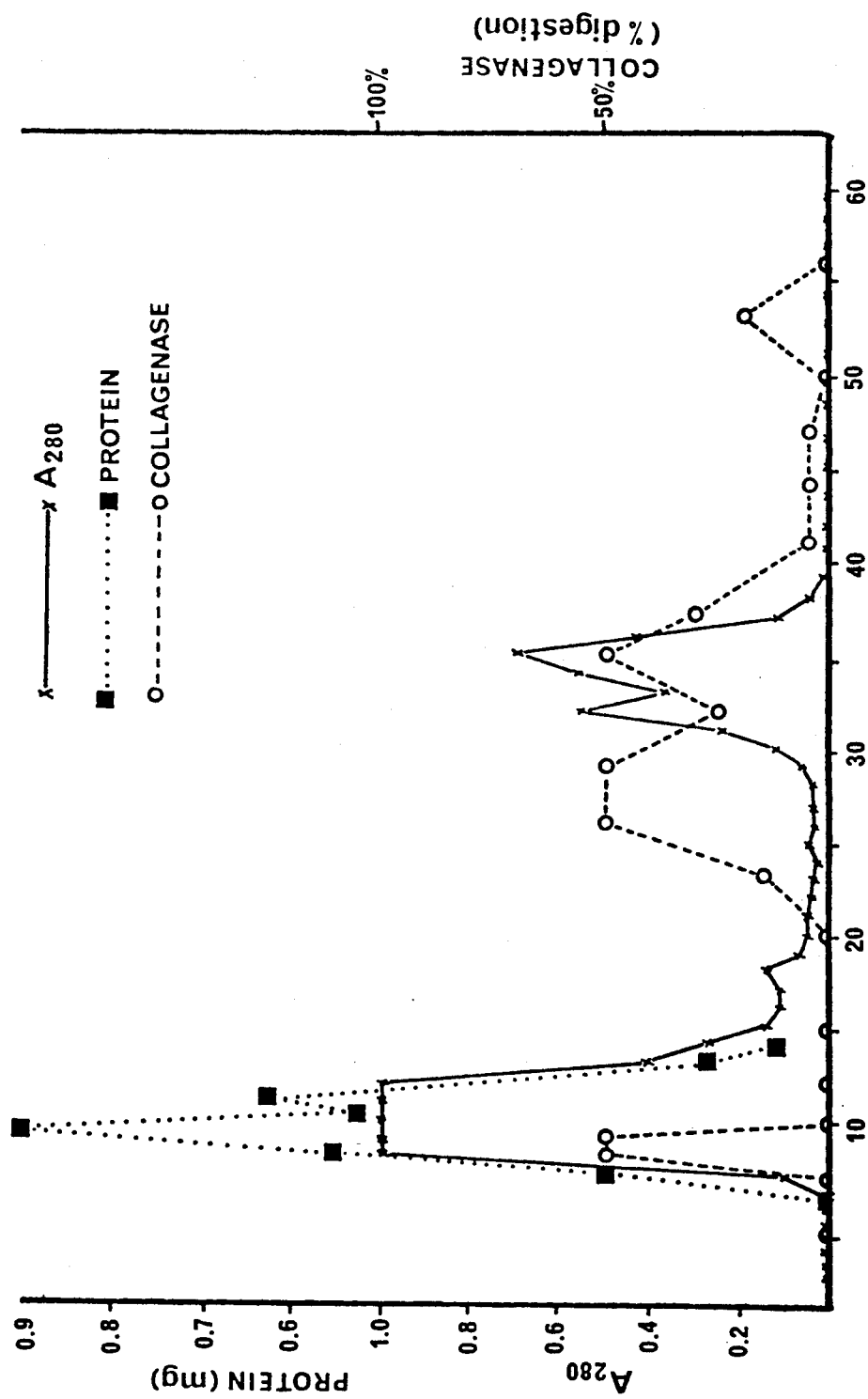

An estimate of the protein content of each fraction was obtained by measurement of its absorbance at 280 nm. Measurement of fractions 0 to 20 by coomassie blue dye showed the A$_{280}$ peak between fractions 7 and 14 to consist of two peaks having maxima at fractions 9 and 11. (See FIG. 3).

Figure 4:
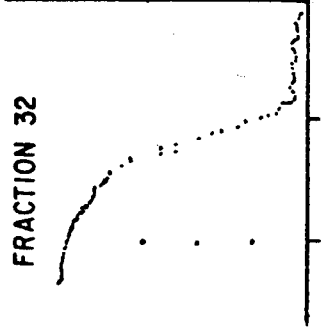
Figure 4:
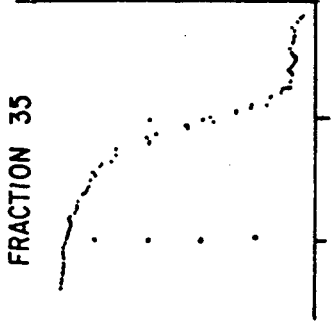
Figure 4:
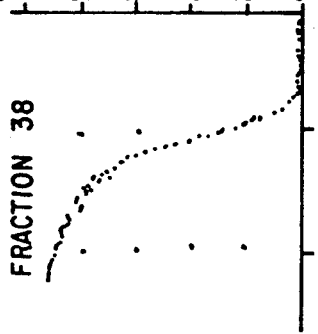
Figure 4:
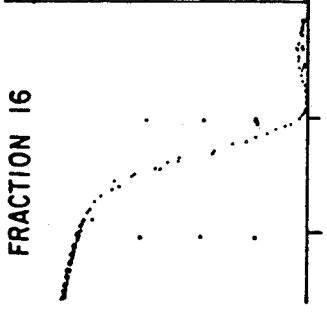
Figure 4:
Figure 4:
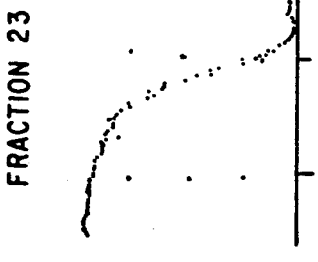
Figure 4:
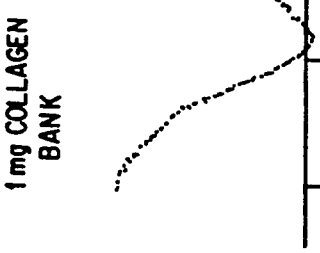
Figure 4:
Figure 4:
Figure 4:
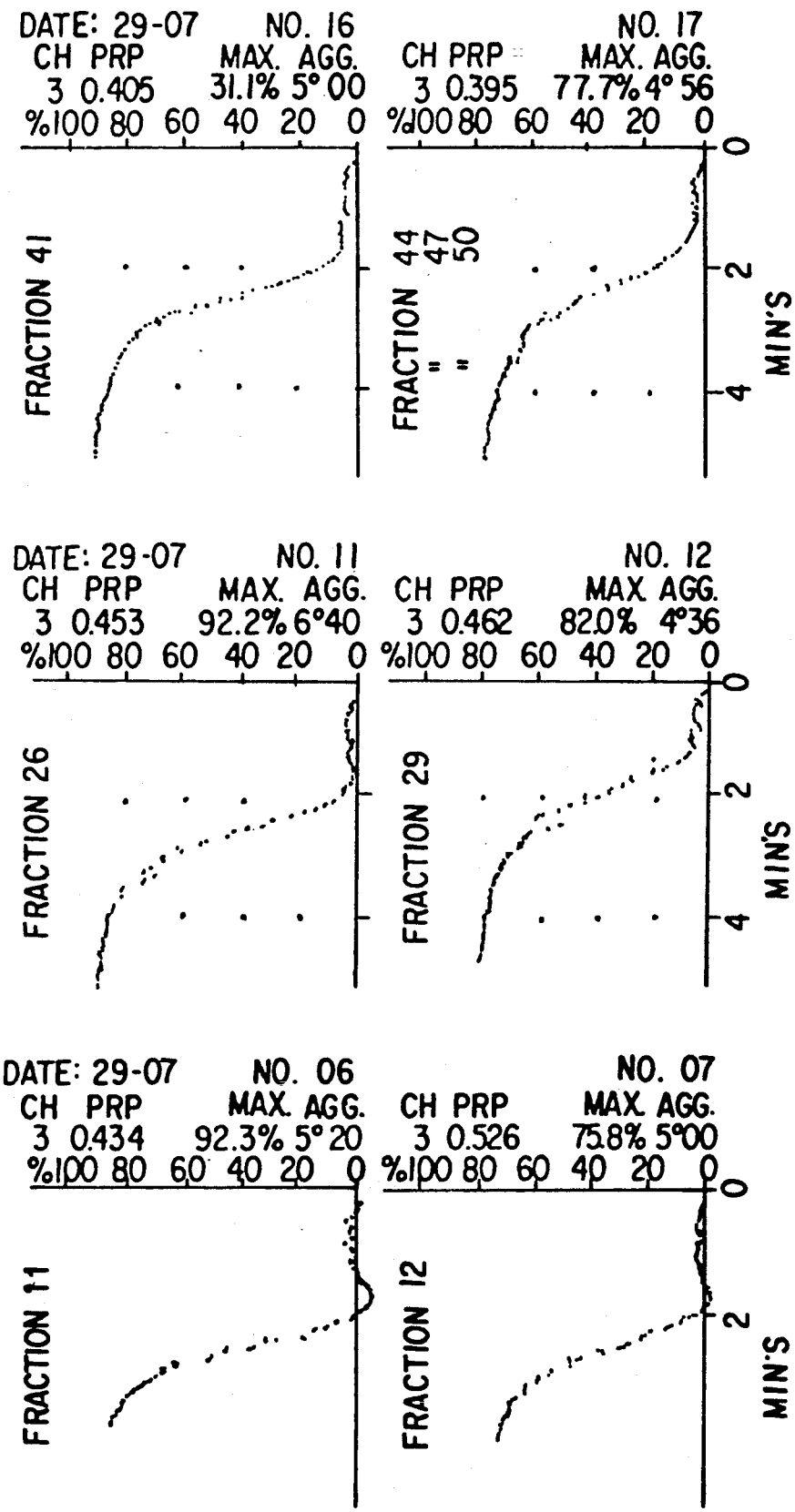

Collangenase activity was assayed by incubation of 100 μl of each fraction with 100 μl 4% gelatin at 37° C. for 3 hours. The samples were then kept on ice for 10 minutes and the degree of liquefaction of the mixture observed by inversion. Controls containing buffer instead of collected fractions were prepared and shown to exhibit no liquefaction. Aliquots of each fraction off the column were also heated at 100° C. for 10 minutes and then assayed in a similar manner for collagenase. Results are shown in FIG. 4. It can be seen that the collagenase activity corresponds with the first protein peak at fractions 8 and 9 and also with the proteins of lower molecular weight between fractions 20 and 40.

Measurement of the ability of each fraction to inhibit collagen-induced platelet aggregation was also studied. Using a platelet aggregometer, the extent of inhibition was studied by adding 50 μl of 4 μg per ml collagen to a mixture of 100 μl fraction and 400 μl platelet rich plasma (300±50×10$^3$ per cu mm). Aggregation in each case was expressed as a percentage of the aggregation induced by a similar amount of collagen when the fraction was replaced by a similar volume of isotonic saline. A cross section of the results obtained are shown in FIG. 4. Fractions 8 and 9 showed complete inhibition of collagen-induced activity. All other fractions showed no significant effect upon collagen-induced platelet aggregation.

Similar results were found with enzyme extracted from *Hirudo medicinalis*.

EXAMPLE 5

That leech collagenase occurs in rhynchobdellid leeches is demonstrated by the following example on the glossi-phoniid *Haementeria ghilianii*.

The entire salivary gland/proboscis complex was dissected from two medium-sized (5 cm) individuals of *Haementeria ghiliannii*. The frozen glands were homogenized with a mortar and pestle to which was added 1.5 ml of distilled water. The total extract was centrifuged for one minute. From both the supernatant and pellet 100 μl samples were added to wells containing 100 μl of 3% gelatin. The solutions were allowed to digest for 24 hours at 22° C. Collagenase activity, i.e. total digestions of the gelatine, occured only in the pellet. The supernatant had no collagenase activity.

EXAMPLE 6

The pharmaceutical potential of leech collagenase as inhibitor of platelet aggregation is demonstrated by the following example:

An adult medicinal leech *Hirudo medicinalis* (2.6 g) was allowed to feed to repletion on the forearm of a human subject. Blood and other parameters were carefully monitored before, during and after the experiment. Baseline blood parameters from a lanced thumb before feeding served as baseline control: clotting occurred in 3½ minutes, and platelet aggregation was clearly visible on smears under the microscope in about half that time.

The leech fed for 58 minutes during which time it sucked 4.5 ml of blood. The wound continued to bleed for more than 3 hours, at a flow rate of 150 μl/min. Blood coming from the wound was sampled at frequent intervals. Clotting time was found to be as follows:

| Time Following Bite | Clotting Time |
| --- | --- |
| 0 mins | 11 mins |
| 5 mins | 7 mins |
| 10 mins | 3½ mins |
| 20 mins | 3½ mins |

These and related data prove that contrary to current views the prolonged bleeding following a leech bite is not due to nirudin (leech antithrombin); with respect to ability to clot (fibrin formation) the blood returns to normal within 10 minutes, but bleeding persists.

Our research shows that the prolonged localised bleeding is due to inhibition of platelet aggregation. In the example when the platelets in the fresh blood were examined by several means, including blood smears on glass slides and a canalyzee which counts platelets; it was found that the platelets showed no tendency to aggregate for more than an hour. With a baseline value of 203,000 platelets per ml of blood, the platelet number was as follows:

| Time Following Bite | Platelet Number |
| --- | --- |
| 1½ mins | 201,000 |
| 20 mins | 202,000 |
| 60 mins | 200,000 |
| 150 mins | 195,000 |

At least after one hour the platelets themselves appear to be normal as demonstrated by the representative observation, at 150 min, that blood several minutes old which had come into contact with skin and old blood had a platelet count of 96,000, a reduction indicative of platelet clumping/aggregation.

Prolonged localized bleeding following a leech bite is best interpreted, in the light of Examples 1-3, as follows. Leech collagenase secreted in the saliva during biting and feeding modifies exposed raw collagen surrounding the damaged vessel wall in such a way as to make it incapable of stimulating aggregation of platelets in passing blood. Collagen is the most potent inducer of platelet aggregation.

The inhibition of platelet aggregation by leech collagenase as described above would be therapeutically very useful, for example in micro-surgery to restore circulation wherever blood is congested such as following surgical implants and tissue flaps and in haematomas.

We claim:

1. A substantially pure collagenase isolated from leech tissue or from leech secretion, said collagenase being capable of (a) causing hydrolytic scission of peptide bonds in the helical regions of undenatured collagen molecules, (b) causing only one cut per chain of said collagen molecules, and (c) digesting gelatin.

2. The collagenase of claim 1 wherein the collagenase is also capable of inhibiting collagen-induced platelet aggregation.

3. The collagenase of claim 2 wherein the molecular weight is from 45 to 55 kdaltons.

4. A method for isolating collagenase according to claim 1, which method comprises the steps of
    (a) fractionating a fluid regurgitated by leeches by means of a gel fractionation; and
    (b) collecting eluate fractions containing said collagenase.

* * * * *